(12) United States Patent
Bohm et al.

(10) Patent No.: US 6,990,849 B2
(45) Date of Patent: Jan. 31, 2006

(54) MICROFLUIDIC ANALYTICAL SYSTEM WITH POSITION ELECTRODES

(75) Inventors: Sebastian Bohm, Inverness (GB); James Iain Rodgers, Lochardil (GB); Alan McNeilage, Inverness (GB); James Moffat, Inverness (GB); Matthias Stiene, Inverness (GB); Tanja Richter, Inverness (GB)

(73) Assignee: Lifescan, Inc., Milipitas, CA (US)

( * ) Notice: Subject to any disclaimer, the term of this patent is extended or adjusted under 35 U.S.C. 154(b) by 0 days.

(21) Appl. No.: 10/811,446

(22) Filed: Mar. 26, 2004

(65) Prior Publication Data

US 2005/0210962 A1 Sep. 29, 2005

(51) Int. Cl.
*G01N 11/00* (2006.01)
*G01N 33/487* (2006.01)
*G01N 15/06* (2006.01)
*G01N 33/00* (2006.01)
*C12M 1/34* (2006.01)

(52) U.S. Cl. .................. 73/53.01; 435/288.5; 422/68.1
(58) Field of Classification Search ............... 73/53.01; 435/288.5; 422/68.1
See application file for complete search history.

(56) References Cited

U.S. PATENT DOCUMENTS

| | | | |
|---|---|---|---|
| 4,169,377 A | 10/1979 | Scheib | 73/304 R |
| 5,033,300 A | 7/1991 | Matsuo et al. | 73/304 R |
| 5,148,708 A | 9/1992 | Murata et al. | 73/304 R |
| 5,226,313 A | 7/1993 | Murata et al. | 73/149 |
| 5,719,556 A | 2/1998 | Albin et al. | 340/618 |
| 5,932,799 A * | 8/1999 | Moles | 73/53.01 |
| 6,748,804 B1 | 6/2004 | Lisec et al. | 73/304 R |
| 2002/0142477 A1 * | 10/2002 | Lewis et al. | 436/151 |
| 2003/0060784 A1 | 3/2003 | Hilgers et al. | 604/272 |
| 2003/0155237 A1 | 8/2003 | Surridge et al. | 204/403.14 |

FOREIGN PATENT DOCUMENTS

| | | |
|---|---|---|
| EP | 0537761 B1 | 4/1993 |
| WO | WO 00/47322 A3 | 8/2000 |
| WO | WO 02/49507 A1 | 6/2002 |
| WO | WO 02/50534 A1 | 6/2002 |
| WO | WO 02/101343 A2 | 12/2002 |
| WO | WO 03/091717 A1 | 11/2003 |

OTHER PUBLICATIONS

WO 01/20271 A1—Abstract—Thomas Lisec, et al., Microsensor for Measuring the Position of Liquids in Capillaries, Published Mar. 22, 2001.
European Patent Office, Munich, Germany; European Patent Search Report Communication dated Jul. 19, 2005 for European Application 05251850.3.

* cited by examiner

*Primary Examiner*—Hezron Williams
*Assistant Examiner*—Tamiko Bellamy

(57) ABSTRACT

A microfluidic analytical system for monitoring an analyte (for example, glucose) in a liquid sample (e.g., ISF) includes an analysis module with at least one micro-channel for receiving and transporting a liquid sample, at least one analyte sensor for measuring an analyte in the liquid sample and at least one position electrode. The analyte sensor(s) and position electrode(s) are in operative communication with the micro-channel. The microfluidic system also includes a meter configured for measuring an electrical characteristic (such as impedance or resistance) of the position electrode(s). Moreover, the measured electrical characteristic is dependent on the position of the liquid sample in the micro-channel that is in operative communication with the position electrode for which an electrical characteristic is measured.

16 Claims, 11 Drawing Sheets

MICROFLUIDIC ANALYTICAL SYSTEM WITH POSITION ELECTRODES

BACKGROUND OF INVENTION

1. Field of the Invention

The present invention relates, in general, to analytical devices and, in particular, to microfluidic analytical systems.

2. Description of the Related Art

In analytical devices based on liquid samples (i.e., fluidic analytical devices), the requisite liquid samples should be controlled with a high degree of accuracy and precision in order to obtain reliable analytical results. Such control is especially warranted with respect to "microfluidic" analytical devices that employ liquid samples of small volume, for example, 10 nanoliters to 10 microliters. In such microfluidic analytical devices, the liquid samples are typically contained and transported in micro-channels with dimensions on the order of, for example, 10 micrometers to 500 micrometers.

The control (e.g., transportation, position detection, flow rate determination and/or volume determination) of small volume liquid samples within micro-channels can be essential in the success of a variety of analytical procedures including the determination of glucose concentration in interstitial fluid (ISF) samples. For example, obtaining reliable results may require knowledge of liquid sample position in order to insure that a liquid sample has arrived at a detection area before analysis is commenced. The relatively small size of the liquid samples and micro-channels in microfluidic analytical devices can, however, render such control problematic.

In the context of analytical systems for blood glucose monitoring, continuous or semi-continuous monitoring systems and methods are advantageous in that they provide enhanced insight into blood glucose concentration trends, the effect of food and medication on blood glucose concentration and a user's overall glycemic control. A challenge of continuous or semi-continuous glucose monitoring systems is that only small volumes of liquid sample (e.g., an ISF liquid sample of about 250 nanoliters) are generally available for measuring a glucose concentration. In addition, it is difficult to transport small volumes of liquid from a target site to an ex vivo glucose monitor with a controlled flow rate and in such a way that the position and total volume of extracted fluid is known.

Still needed in the field, therefore, is a microfluidic analytical system that enables small volume liquid sample control and otherwise alleviate the problems described above.

SUMMARY OF INVENTION

Microfluidic analytical systems according to embodiments of the present invention enable small volume liquid sample control and otherwise alleviate the problems described above.

A microfluidic analytical system for monitoring an analyte (e.g., glucose) in a liquid sample (e.g., ISF) according to an embodiment of the present invention includes an analysis module with at least one micro-channel for receiving and transporting a liquid sample, at least one analyte sensor for measuring an analyte in the liquid sample and at least one position electrode. The analyte sensor(s) and position electrode(s) are in operative communication with the micro-channel.

The microfluidic analytical system also includes a meter configured for measuring an electrical characteristic (e.g., impedance or resistance) of the position electrode(s). For example, the meter may measure an electrical characteristic (e.g., resistance) between two ends of a single position electrode or measure an electrical characteristic (e.g., impedance) between two position electrodes.

Moreover, in embodiments of microfluidic analytical systems according to embodiments of the present invention, the measured electrical characteristic is dependent on the position of the liquid sample in the micro-channel that is in operative communication with the position electrode for which an electrical characteristic is measured. For example, a change in measured impedance can be dependent on the position of the front of a conducting liquid sample in a micro-channel with respect to one or more position electrodes.

Since microfluidic analytical devices according to embodiments of the present invention include a meter that measures an electrical characteristic that is dependent on liquid sample position in the micro-channel, the measurements enable accurate liquid sample position detection, liquid sample flow rate determination and/or liquid sample volume determination.

BRIEF DESCRIPTION OF DRAWINGS

A better understanding of the features and advantages of the present invention will be obtained by reference to the following detailed description that sets forth illustrative embodiments, in which principles of the invention are utilized, and the accompanying drawings of which.

DETAILED DESCRIPTION OF THE INVENTION

Figure 1:
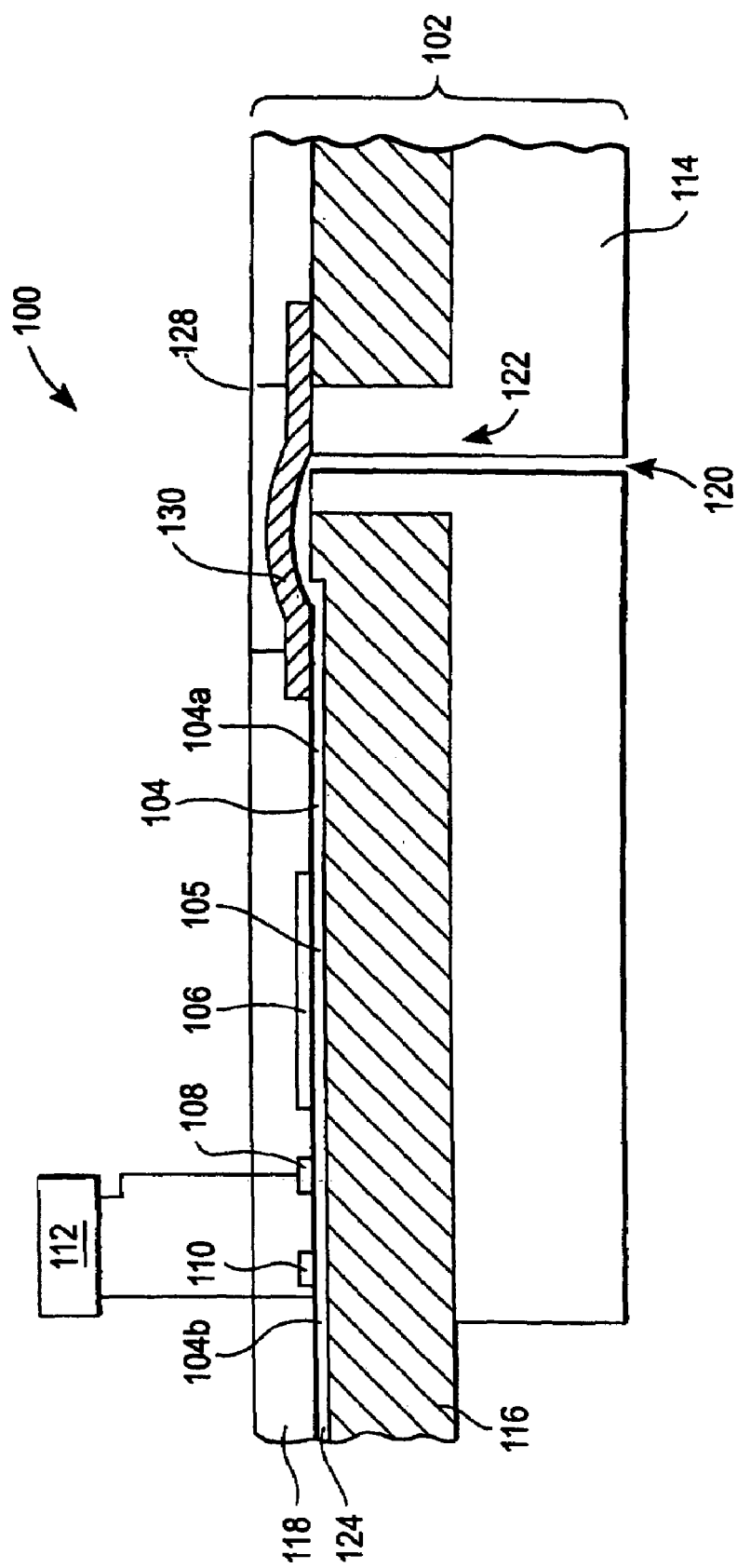
FIG. 1 is a simplified cross-sectional side view and schematic representation of a microfluidic analytical system according to an exemplary embodiment of the present invention.

FIGS. 1–4 depict a microfluidic analytical system 100 for determining an analyte (e.g., detecting the analyte and/or measuring the concentration of the analyte) in a liquid sample according to an exemplary embodiment of the present invention.

Microfluidic analytical system 100 includes an analysis module 102 with a micro-channel 104 for receiving and transporting a liquid sample (e.g., an ISF sample extracted from a dermal tissue target site), an analyte sensor 106 (e.g., an electrochemical analyte sensor or photometric analyte sensor) for measuring an analyte (e.g., glucose) in the liquid sample, and first and second position electrodes 108 and 110. In the embodiment of FIGS. 1–4, micro-channel 104 includes a pre-sensor micro-channel portion 104a and a post-sensor micro-channel portion 104b. Microfluidic analytical system 100 also includes a sensor chamber 105, within which analyte sensor 106 is disposed.

Microfluidic analytical system 100 further includes a meter 112 for measuring impedance between first position electrode 108 and second position electrode 110, with the measured impedance being dependent on the position of a liquid sample (not shown in FIGS. 1–4) in micro-channel 104.

In general, measuring impedances, or ohmic resistances, between position electrodes in embodiments of the present invention can be accomplished by applying a voltage therebetween and measuring the resulting current. Either a constant voltage or an alternating voltage can be applied between the position electrodes and the resulting direct current (DC) or alternating current (AC), respectively, measured. The resulting DC or AC current can then be used to calculate the impedance or ohmic resistance. Furthermore, one skilled in the art will recognize that measuring an impedance can involve measuring both an ohmic drop (i.e., resistance [R] in Ohms or voltage/current) and measuring capacitance (i.e., capacitance in Farads or coulombs/volt). In practice, impedance can be measured, for example, by applying an alternating current to the position electrode(s) and measuring the resulting current. At different frequencies of alternating current, either resistive or capacitive effects prevail in determining the measured impedance. The pure resistive component can prevail at lower frequencies while the pure capacitive component can prevail at higher frequencies. To distinguish between the resistive and capacitive components, the phase difference between the applied alternating current and the measured resulting current can be determined. If there is zero phase shift, the pure resistive component is prevailing. If the phase shift indicates that the current lags the voltage, then the capacitive component is significant. Therefore, depending on the frequency of an applied alternating current and position electrode configuration, it can be beneficial to measure either resistance or a combination of resistance and capacitance.

In the embodiment of FIGS. 1–4, impedance measurements can be performed by, for example, applying an alternating voltage between first position electrode 108 and second position electrode 110 and measuring the resulting alternating current. Since first position electrode 108 and second position electrode 110 are a portion of a capacitor (along with any substance [e.g., air or a liquid sample] within micro-channel 104 between the first and second position electrodes and any layers that may be separating the position electrodes from direct contact with the substance), the measured current can be used to calculate the impedance. The presence or absence of a liquid sample in micro-channel 104 between the first and second position electrodes will affect the measured current and impedance.

The frequency and amplitude of the alternating voltage applied between the first and second position electrodes can be predetermined such that the presence of a liquid sample between the first and second position electrodes can be detected by a significant increase in measured current.

With respect to the measurement of impedance or resistance, the magnitude of the applied voltage can be, for example, in range from about 10 mV to about 2 volts for the circumstance of an ISF liquid sample and carbon-based or silver-based ink position electrodes. The lower and upper limits of the applied voltage range are dependent on the onset of electrolysis or electrochemical decomposition of the liquid sample. In the circumstance that an alternating voltage is employed, the alternating voltage can be applied, for example, at a frequency that results in a negligible net change in the liquid sample's properties due to any electrochemical reaction. Such a frequency range can be, for example, from about 10 Hz to about 100 kHz with a voltage waveform symmetrical around 0 Volts (i.e., the RMS value of the alternating voltage is approximately zero).

As depicted in a simplified manner in FIG. 1, analyte sensor 106, first position electrode 108 and second position electrode 110 are each in operative communication with micro-channel 104. It should be noted that position electrodes employed in embodiments of the present invention can be formed of any suitable conductive material known to those skilled in the art, including conductive materials conventionally used as analytical electrode materials and, in particular, conductive materials known as suitable for use in flexible circuits, photolithographic manufacturing techniques, screen printing techniques and flexo-printing techniques. Suitable conductive materials include, for example, carbon, noble metals (e.g., gold, platinum and palladium), noble metal alloys, conductive potential-forming metal oxides and metal salts. Position electrodes can be formed, for example, from conductive silver ink, such as the commercially available conductive silver ink Electrodag 418 SS.

Figure 2:
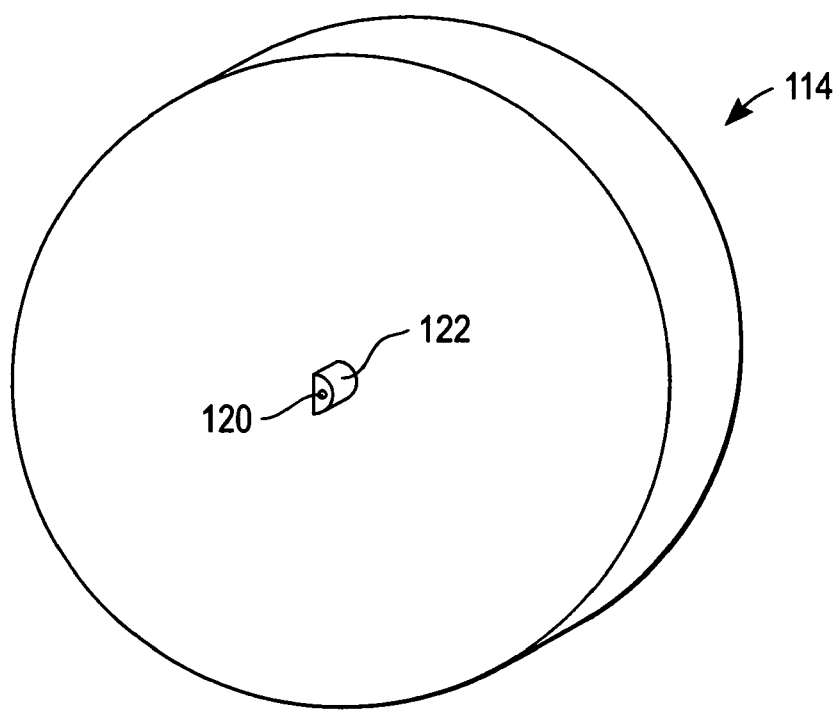
FIG. 2 is a simplified perspective view of a molded plug of the microfluidic analytical system of FIG. 1.
Figure 3:
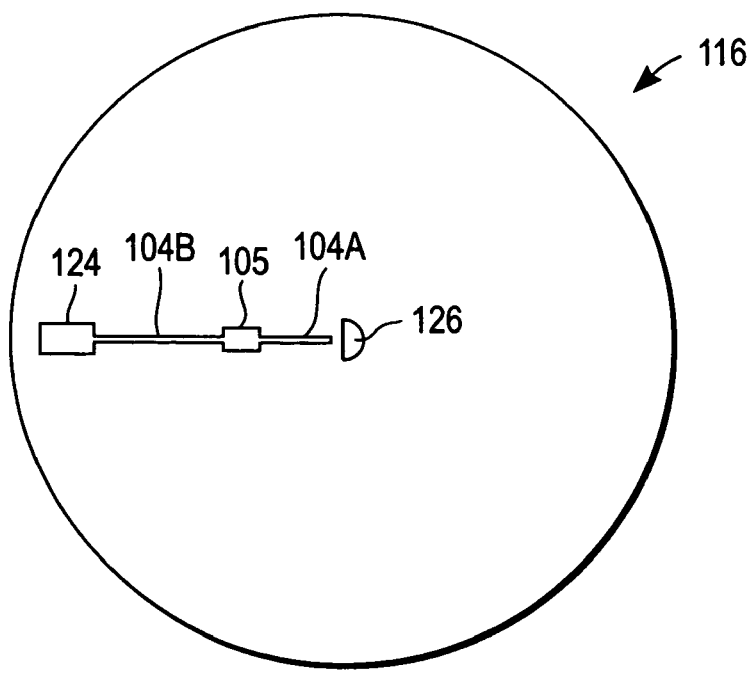
FIG. 3 is a simplified top view of a micro-channel disc of the microfluidic analytical system of FIG. 1.
Figure 4:
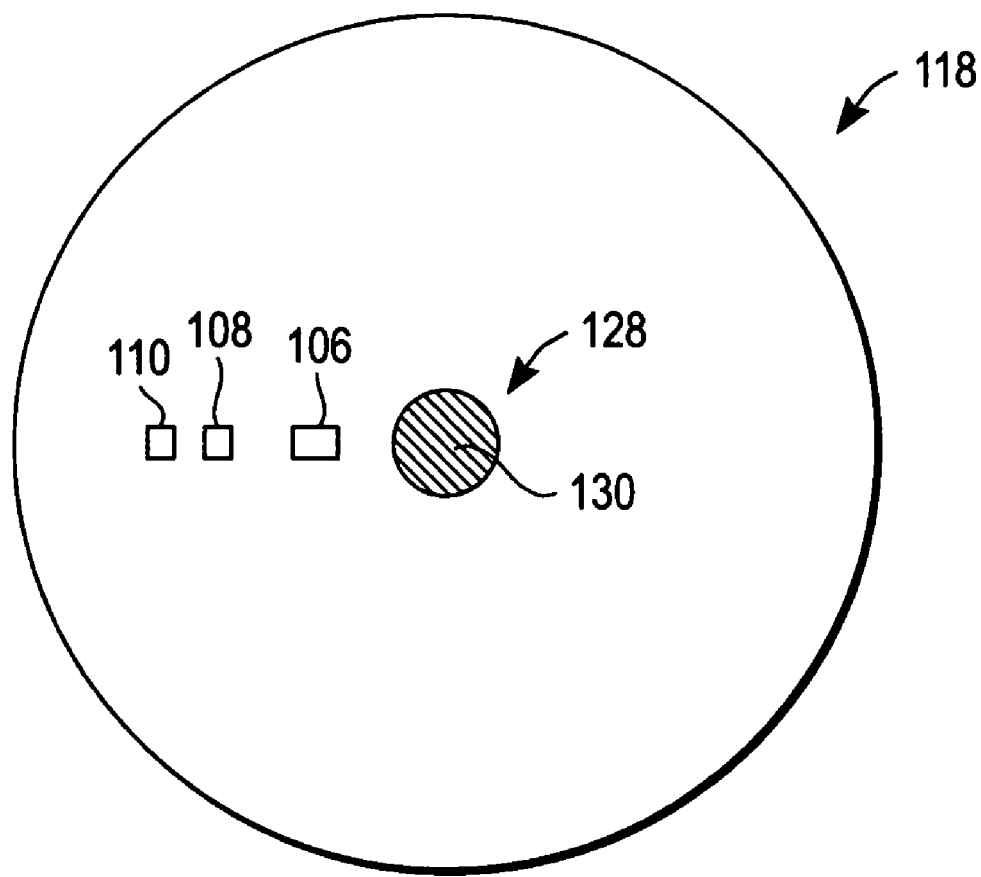
FIG. 4 is a simplified bottom view of a laminate layer of the microfluidic analytical system of FIG. 1.

In the embodiment of FIGS. 1–4, analysis module 102 further includes a molded plug 114, a micro-channel disc 116 and a laminate layer 118 (depicted individually in FIGS. 2, 3 and 4, respectively). Analysis module 102 can be constructed by, for example, interfacing micro-channel disc 116 with laminate layer 118 and molded plug 114.

Molded plug 114 includes an inlet channel 120 and a registration pole 122. Micro-channel disc 116 is configured to define (along with laminate layer 118) a liquid sample waste reservoir 124, as well as the aforementioned micro-channel 104 and sensor chamber 105. In addition, micro-channel disc 116 includes a registration hole 126 (see, for example, FIG. 3).

Laminate layer 118 includes an access hole 128, a membrane valve 130, and in the embodiment of FIGS. 1–4, the aforementioned analyte sensor 106 and first and second position electrodes 108 and 110.

Micro-channel 104 has cross-sectional dimensions perpendicular to a direction of fluid flow (i.e., height and width) in the range of about 10 micrometers to about 500 micrometers. Typical liquid sample volumes to be handled in a micro-channel(s) of embodiments of the present invention are on the order of about 10 nanoliters to about 10 microliters. In this respect, the term "handled" is in reference to the transportation of various liquid sample volumes including, but not limited to, isolated liquid sample volumes extracted from a target site (e.g., isolated volumes in the range of 50 nl to 250 nl), the minimum liquid sample volume required by an analyte sensor (for example, 50 nl), and the total liquid sample volume that is conducted through a micro-channel throughout the useful lifetime of a microfluidic analytical system (for example, a total volume of approximately 10 micro-liters).

Registration pole 122 of molded plug 114 is employed during manufacturing of microfluidic analytical system 100 to ensure adequate alignment (i.e., registration) of molded plug 114 and micro-channel disc 116. For example, such alignment must insure that analyte sensor 106 is operatively aligned with sensor chamber 105 and that first and second position electrodes 108 and 110 are aligned with post-sensor micro-channel channel 104b. During manufacturing, laminate layer 118 can be aligned with micro-channel disc 116 using registration features included in laminate layer 118 and/or micro-channel disc 116 (not shown) or by optical verification.

Registration hole 126 of micro-channel disc 116 is depicted as having a half circle shape and extending entirely through micro-channel disc 116. Registration pole 122 has a shape and size that are complementary to registration hole 126, thus providing for micro-channel disc 116 to securely interface with the molded plug 114, as depicted in FIG. 1. The use of half circle shapes for both registration hole 126 and registration pole 122 beneficially limits the rotational freedom of a combined molded plug 114 and micro-channel disc 116. It should be noted that alternative shapes other than a half circle can also be used.

Figure 5:
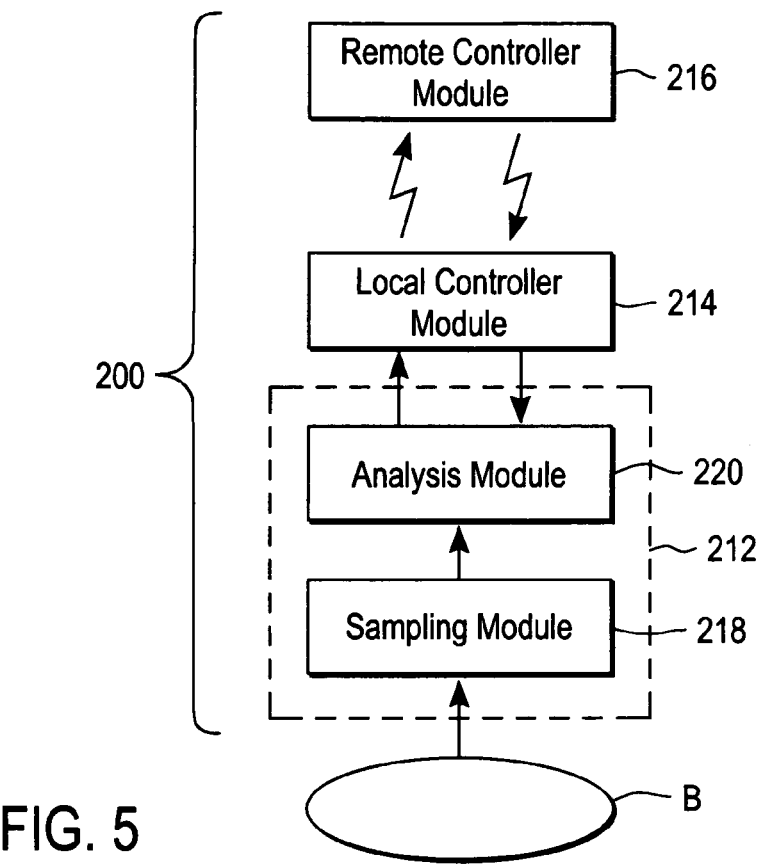
FIG. 5 is a simplified block diagram depicting a system for extracting a bodily liquid sample and monitoring an analyte therein, with which embodiments of microfluidic analytical systems according to the present invention can be employed.

Although not depicted in FIGS. 1–4, laminate layer 118 includes electrical connections to electrically connect analyte sensor 106 to external apparatus (such as a local controller module as described with respect to FIG. 5 below) and to connect first and second position electrodes 108 and 110 to meter 112. Such electrical connections can include, for example, conductive traces and electrical contact pads.

It is contemplated that a liquid sample (e.g., an ISF sample) will be transported to inlet channel 120 by suitable means, such as a sampling module as described below with respect to FIG. 5. Flow of liquid sample through inlet channel 120 is controlled by membrane valve 130. It should be noted that other types of valves, besides membrane valves, can be used and are well know to one skilled in the art.

In an embodiment of FIG. 1, membrane valve 130 is deformable and made of an elastomeric material in a dome shape. When membrane valve 130 is an undeformed condition, a liquid sample may flow past membrane valve 130 and fill pre-sensor micro-channel portion 104a. However, when membrane valve 130 is initially deformed (for example, by the application of pressure via access hole 128), it occludes inlet channel 120 and prevents liquid sample from flowing therethrough. In addition, further deformation of membrane valve 130 pushes liquid sample through pre-sensor micro-channel portion 104a and into sensor chamber 105. The movement of liquid sample past membrane valve 130 (i.e., from inlet channel 120 to pre-sensor micro-channel portion 104a) can be controlled by the amount of pressure applied in deforming membrane valve 130. Typical liquid sample flow rates into micro-channel 104 are in the range of about 10 nanoliters per minute to about 1000 nanoliters per minute.

First and second position electrodes 108 and 110, along with meter 112, can be used to determine the liquid sample position within micro-channel 104, the flow rate of a liquid sample and/or the volume of an extracted liquid sample to help control the depression of membrane valve 130. It is beneficial to determine liquid sample position in order to ascertain when a minimum amount of liquid sample has been collected into analysis module 102 to initiate analyte determination. It can also be beneficial to determine liquid sample flow rate and/or the total amount of liquid sample that has entered microfluidic analytical system 100 in order to control membrane valve 130 in a manner that facilitates semi-continuous stopped flow measurements (i.e., measurements taken with liquid sample flow momentarily halted and that result in a predetermined number of measurements per unit time [typically in the range of 4 to 10 measurements per hour] rather than a continuous measurement) over a predetermined time periods. In addition, determining liquid sample flow rate and the total amount of liquid sample enables sensor lag compensation. Furthermore, analyte sensor 106 may be sensitive to flow rate. Therefore, the use of first and second position electrodes and meter 112 allows system 100 to more accurately determine an analyte over an extended period of time such as, for example, about 8 hours.

In the embodiment of FIGS. 1–4, analyte sensor 106 is disposed within sensor chamber 105. Analyte sensor 106 can be any suitable sensor known to one skilled in the art. For the circumstance where the analyte of interest is glucose, analyte sensor 106 can be an electrochemical glucose sensor that measures a current proportional to glucose concentration. More particularly, analyte sensor 106 can be, for example, an electrochemical glucose sensor that measures current under stopped flow conditions (i.e., flow rates at or near zero during measurement) and with glucose being consumed within sensor chamber 105. Examples of analyte sensors that may be used in embodiments of the present invention include, but not limited to, electrochemical-based and photometric-based analyte sensors. Electrochemical-based analyte sensors include, for example, amperometric, potentiometric and coulometric analyte sensors. Photometric-based analyte sensors include, for example, transmission, reflectance, calorimetric, fluorometric, scattering and absorbance analyte sensors.

After an analyte in a liquid sample has been determined by analyte sensor 106, the liquid sample is transported to post-sensor micro-channel portion 104b.

One skilled in the art will recognize that analyte monitoring systems according to embodiments of the present invention can be employed, for example, as a subsystem in a variety of devices. For example, embodiments of the present invention can be employed as an analysis module of system 200 depicted in FIG. 5. System 200 is configured for extracting a bodily liquid sample (e.g., an ISF sample) and monitoring an analyte (e.g., glucose) therein. System 200 includes a disposable cartridge 212 (encompassed within the dashed box), a local controller module 214 and a remote controller module 216.

In system 200, disposable cartridge 212 includes a sampling module 218 for extracting the bodily liquid sample (namely, an ISF sample) from a body (B, for example, a user's skin layer) and an analysis module 200 for measuring an analyte (i.e., glucose) in the bodily fluid. Sampling module 218 can be any suitable sampling module known to those of skill in the art, while analysis module 220 can be a microfluidic analytical system according to embodiments of the present invention. Examples of suitable sampling modules are described in International Application PCT/GB01/05634 (published as WO 02/49507 A1 on Jun. 27, 2002) and U.S. patent application Ser. No. 10/653,023, which is hereby fully incorporated herein by reference. However, in system 200, sampling module 218 is configured to be disposable since it is a component of disposable cartridge 212.

Figure 6:
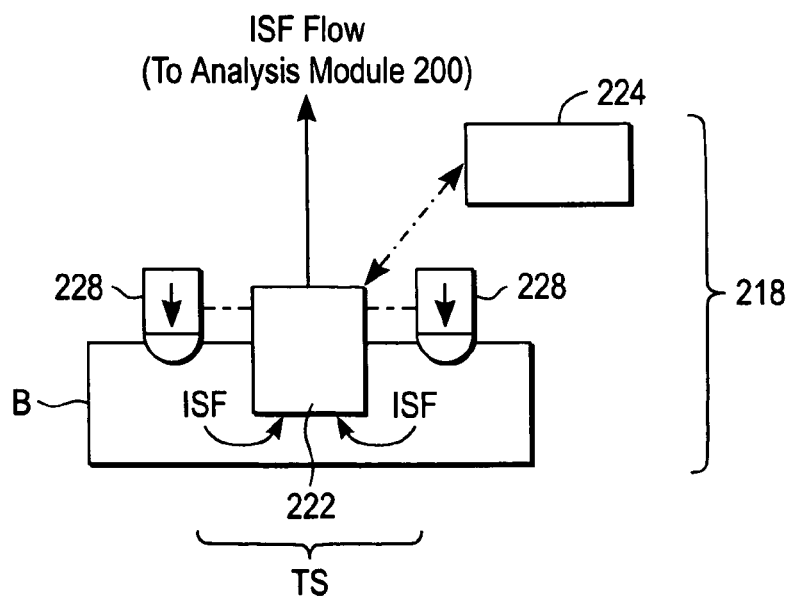
FIG. 6 is a simplified schematic diagram of the sampling module of FIG. 5 being applied to a user's skin layer, with the dashed arrow indicating a mechanical interaction and the solid arrows indicating ISF flow or, when associated with element 228, the application of pressure.

As depicted in FIG. 6, the sampling module 218 of system 200 is an ISF sampling module that includes a penetration member 222 for penetrating a target site (TS) of body B and extracting an ISF sample, a launching mechanism 224 and at least one pressure ring 228. Sampling module 218 is adapted to provide a continuous or semi-continuous flow of ISF to analysis module 220 for the monitoring (e.g., concentration measurement) of an analyte (such as glucose) in the ISF sample.

During use of system 200, penetration member 222 is inserted into the target site (i.e., penetrates the target site) by operation of launching mechanism 224. For the extraction of an ISF sample from a user's skin layer, penetration member 222 can be inserted to a maximum insertion depth in the range of, for example, 1.5 mm to 3 mm. In addition, penetration member 222 can be configured to optimize extraction of an ISF sample in a continuous or semi-continuous manner. In this regard, penetration member 222 can include, for example, a 25 gauge, thin-wall stainless steel needle (not shown in FIG. 5 or 6) with a bent tip, wherein a fulcrum for the tip bend is disposed between the needle's tip and the needle's heel. Suitable needles for use in penetration members are described in U.S. patent application Ser. No. 10/185,605 (published as U.S. 2003/0060784 A1 on Mar. 27, 2003). Furthermore, further details regarding system 200 are in U.S. patent application Ser. No. 10/718,818.

Figure 7:
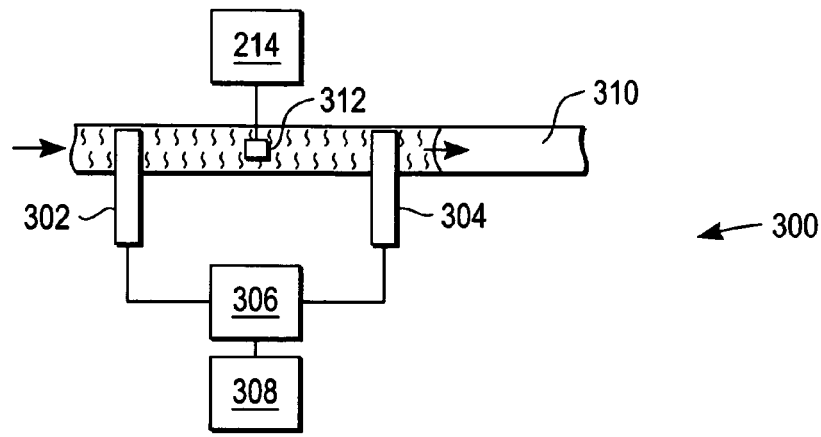
FIG. 7 is a simplified schematic diagram of a position electrode, micro-channel, analyte sensor and meter configuration for use in embodiments of microfluidic analytical systems according to the present invention.

In the embodiment of FIGS. 1–4, first and second position electrodes 108 and 110 and meter 112 are configured such that both the first and second position electrodes are "downstream" of analyte sensor 106 with respect to micro-channel 104. However, other suitable configurations can be employed. For example, FIG. 7 is a simplified schematic diagram of a position electrode, micro-channel, analyte sensor and meter configuration 300 for use in embodiments of microfluidic analytical systems according to the present invention. Configuration 300 includes first position electrode 302, second position electrode 304, electrical impedance meter 306, timer 308, micro-channel 310 and analyte sensor 312. In the configuration of FIG. 7, wavy lines depict a liquid sample (e.g., an ISF, blood, urine, plasma, serum, buffer or reagent liquid sample) within micro-channel 310.

Configuration 300 can be used to determine the position or flow rate of a liquid sample in micro-channel 310. In the configuration of FIG. 7, analyte sensor 312 is located in-between first position electrode 302 and second position electrode 304. Electrical impedance meter 306 is adapted for measuring an electrical impedance between first position electrode 302 and second electrode 304. Such a measurement can be accomplished by, for example, employing a voltage source to impose either a continuous or alternating voltage between first position electrode 302 and second position electrode 304 such that an impedance resulting from a conducting path formed by a liquid sample within micro-channel 310 and between first position electrode 302 and second position electrode 304 can be measured, yielding a signal indicative of the presence of the liquid sample.

Furthermore, when electrical impedance meter 306 measures a change in impedance due to the presence of a liquid sample between the first and second position electrodes, a signal can be sent to timer 308 to mark the time at which liquid is first present between the first and second position electrodes. When the measured impedance indicates that the liquid sample has reached the second position electrode, another signal can be sent to timer 308. The difference in time between when a liquid sample is first present between the first and second position electrodes and when the liquid sample reaches the second position electrode can be used to determine liquid sample flow rate (given knowledge of the volume of micro-channel 310 between the first and second position electrodes). Furthermore, knowledge of liquid sample flow rate and/or liquid sample position can be used to determine total liquid sample volume. In addition, a signal denoting the point in time at which a liquid sample arrives at second position electrode 304 can also be sent to a local controller module (e.g., local controller module 214 of FIG. 5) for use in determining the proper deformed state for membrane valve 130.

Figure 8A:
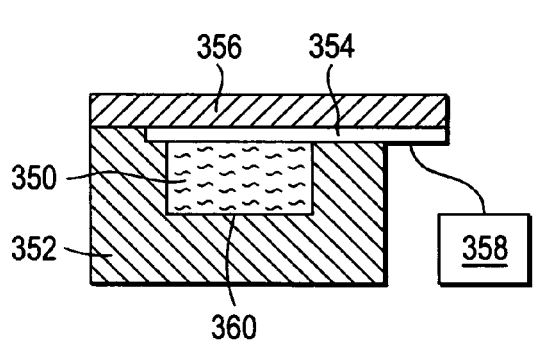
FIG. 8A is a simplified cross-sectional and schematic diagram illustrating a manner in which a position electrode can be exposed to a micro-channel in embodiments of microfluidic analytical systems according to the present invention.

FIG. 8A is a simplified cross-sectional and schematic diagram illustrating a manner in which a position electrode can be in operative communication with a micro-channel in embodiments of microfluidic analytical systems according to the present invention. FIG. 8A depicts a micro-channel 350 (in cross-section), a micro-channel disc 352, a position electrode 354, a laminate layer 356 and a meter 358. In the configuration of FIG. 8A, position electrode 354 is in operative communication with the micro-channel 350 such that a surface 360 of position electrode 354 is exposed to liquid sample (depicted by the wavy lines in FIG. 8A) in micro-channel 350.

In the embodiment of FIG. 8A (and other embodiments of the present invention), micro-channel disc 352 and laminate layer 356 are made of electrically insulating material such as, for example, polymeric insulating materials (e.g., polystyrene, silicone rubber, PMMA, polycarbonate or PEEK) and non-polymeric insulating materials such as, for example, glass.

Figure 8B:
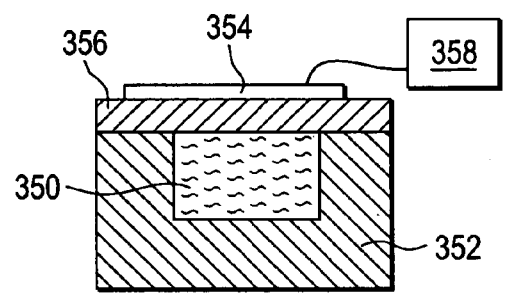
FIG. 8B is a simplified cross-sectional and schematic diagram illustrating a manner in which a position electrode is separated from a micro-channel by an insulating layer in embodiments of microfluidic analytical systems according to the present invention.

FIG. 8B is a simplified cross-sectional and schematic diagram (employing the same labeling numerals as FIG. 8A) illustrating another manner by which a position electrode can be in operative communication with a micro-channel in embodiments of microfluidic analytical systems according to the present invention. FIG. 8B depicts a micro-channel 350 (in cross-section), a micro-channel disc 352, a position electrode 354, a laminate layer 356 and a meter 358. In the configuration of FIG. 8b, position electrode 354 is in operative communication with the micro-channel 350 but separated from micro-channel 350 by an insulating layer, namely a portion of laminate layer 356. A benefit of the manner depicted in FIG. 8B is that there is no direct contact between liquid sample in micro-channel 350 and position electrode 354 and, consequently, no electrolysis or electrochemical decomposition of the liquid sample due to position electrode 354 can occur.

Figure 9:
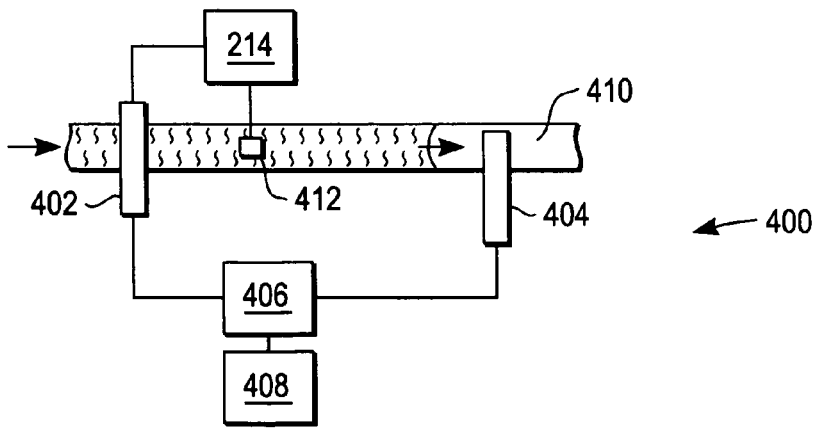
FIG. 9 is simplified schematic diagram of another position electrode, micro-channel, analyte sensor and meter configuration for use in embodiments of microfluidic analytical systems according to the present invention illustrating a manner by which a position detector can be in electrical communication with an analyte sensor.

FIG. 9 is simplified schematic diagram of another micro-channel, analyte sensor and position electrode configuration 400 for use in embodiments of microfluidic analytical systems according to the present invention. Configuration 400 includes first position electrode 402, second position electrode 404, electrical impedance meter 406, timer 408, micro-channel 410 and analyte sensor 412. In the configuration of FIG. 9, wavy lines depict a liquid sample (e.g., an ISF, blood, urine, plasma, serum, buffer or reagent liquid sample) within micro-channel 410.

In the embodiment of FIG. 9, both first position electrode 402 and analyte sensor 412 are in operative communication with local controller module 214. In this manner first position electrode can serve both as a position electrode and as a reference electrode for analyte sensor 412 (assuming that analyte sensor 412 is an electrochemical-based analyte sensor). Furthermore, it should be noted that electrical impedance meter 406 and timer 408 may be incorporated into local controller module 214.

An advantage of the configuration of FIG. 9 is a reduced complexity that is achieved by using the first position electrode as both a position electrode and a reference electrode for analyte sensor 412. In the configuration of FIG. 9, first position electrode 402 can, for example, be manufactured of a material that results in a stable electrical potential between the first position electrode and the liquid sample. In the circumstance that the liquid sample is an ISF liquid sample, the first position electrode can be formed of chlorinated silver (Ag/AgCl).

Figure 10:
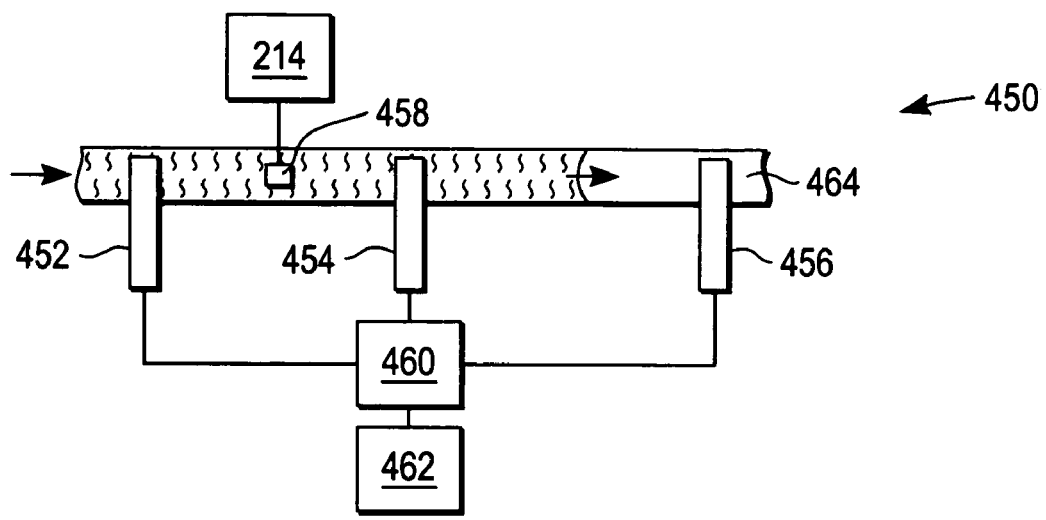
FIG. 10 simplified schematic diagram of yet another position electrode, micro-channel, analyte sensor and meter configuration for use in embodiments of microfluidic analytical systems according to the present invention showing the use of three position electrodes.

FIG. 10 is a simplified schematic diagram of yet another position electrode, micro-channel, analyte sensor and meter configuration 450 for use in embodiments of microfluidic analytical systems according to the present invention. Configuration 450 includes first, second and third position electrodes 452, 454 and 456, respectively, an analyte sensor 458, an electrical impedance meter 460, timer 462, and micro-channel 464. Electrical impedance meter 460 is configured to measure the electrical impedance between any two of the first, second and third position electrodes.

Configuration 450 differs from configurations 300 and 400 in that configuration 450 includes three position electrodes. The inclusion of three position electrodes provides for an improved ability to accurately detect the position and flow rate of a liquid sample within micro-channel 464. For example, the use of two position electrodes enables the detection of a single bolus (i.e., the volume contained in a micro-channel between the two position electrodes). However, the use of three (or more) position electrodes enables the detection of multiple boluses as the liquid sample sequentially passes the three (or more) position electrodes.

Figure 11:
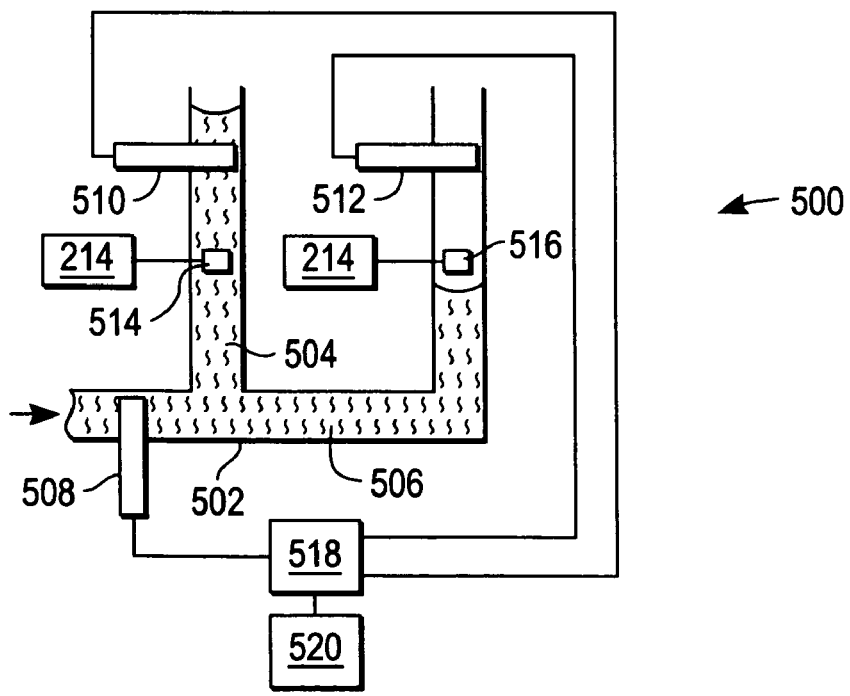
FIG. 11 is simplified schematic diagram of a position electrode, main micro-channel, branch micro-channels, analyte sensor and meter configuration for use in embodiments of microfluidic analytical systems according to the present invention.
Figure 12:
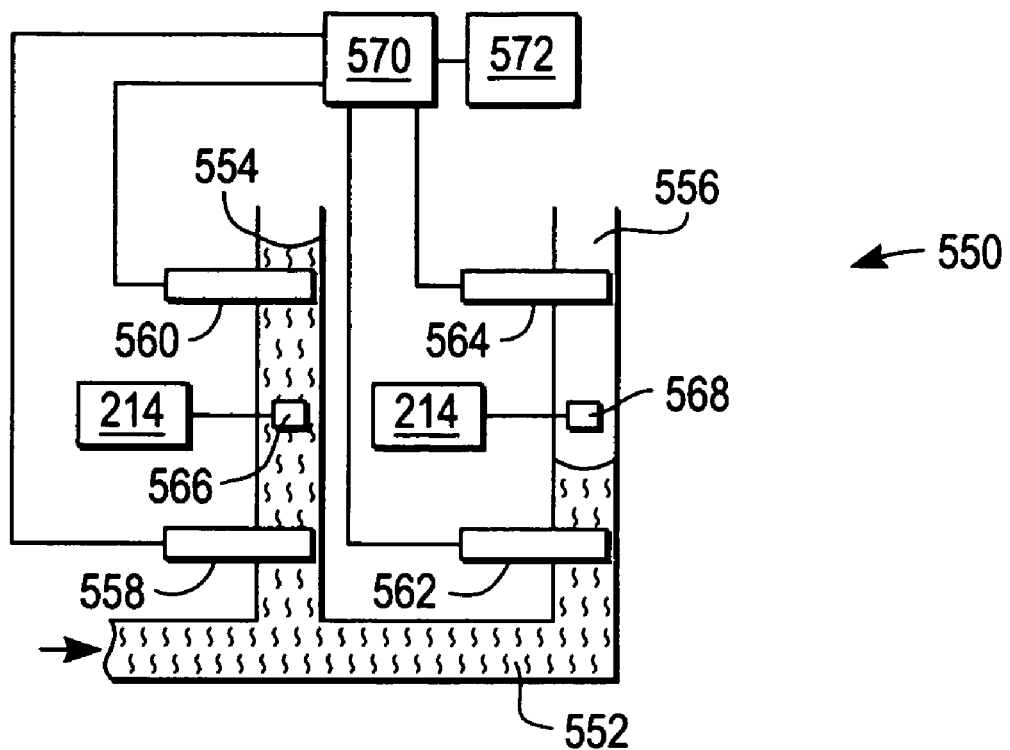
FIG. 12 is simplified schematic diagram of another position electrode, main micro-channel, branch micro-channels, analyte sensor and meter configuration for use in embodiments of microfluidic analytical systems according to the present invention.

FIG. 11 is simplified schematic diagram of a position electrode, micro-channel (comprised of a main micro-channel and two branch micro-channels), analyte sensor and meter configuration 500 for use in embodiments of microfluidic analytical systems according to the present invention. Configuration 500 includes a micro-channel comprised of main micro-channel 502, first branch micro-channel 504 and second branch micro-channel 506. Configuration 500 also includes first position electrode 508 (in operative communication with main micro-channel 502), second position electrode 510 (in operative communication with first branch micro-channel 504) and third position electrode 512 (in operative communication with second branch micro-channel 506).

Furthermore, configuration 500 includes a first analyte sensor 514 (in operative communication with first branch micro-channel 504) and a second analyte sensor 516 (in operative communication with second branch micro-channel 506), a meter 518 and timer 520. Meter 518 is configured to measure an electrical characteristic (e.g., impedance) between the first position electrode and either of the second and third position electrodes.

It is envisioned that configuration 500 will be employed in a device that includes liquid handling means for selectively directing a liquid sample from main micro-channel 502 to either of first and second branch micro-channels 504 and 506. Examples of such liquid handling means include, but are not limited to, active valves, passive valves, capillary breaks, air pressure barriers and hydrophobic patches.

Configuration 500 can be employed to detect the position of a liquid sample in either first branch micro-channel 504 (by employing meter 518 to measure an electrical characteristic between first position electrode 508 and second position electrode 510) or second branch micro-channel 506 (by employing meter 518 to measure an electrical characteristic between first position electrode 508 and third position electrode 512). Such detection(s) can be employed to control liquid sample flow and the determination of an analyte in the liquid sample by either first analyte sensor 514 or second analyte sensor 516.

FIG. 11 is simplified schematic diagram of another position electrode, micro-channel (comprised of a main micro-channel and two branch micro-channels), analyte sensor and meter configuration 550 for use in embodiments of microfluidic analytical systems according to the present invention. Configuration 550 includes a micro-channel comprised of main micro-channel 552, first branch micro-channel 554 and second branch micro-channel 556. Configuration 550 also includes first and second position electrodes 558 and 560 (in operative communication with first branch micro-channel 554), and third and fourth position electrodes 562 and 564 (in operative communication with second branch micro-channel 556).

Furthermore, configuration 550 includes a first analyte sensor 566 (in operative communication with first branch micro-channel 554) and a second analyte sensor 568 (in operative communication with second branch micro-channel 556), a meter 570 and timer 572. Meter 570 is configured to measure an electrical characteristic (e.g., impedance) between either of the first and second position electrodes and the third and fourth position electrodes.

It is envisioned that configuration 550 will be employed in a device that includes liquid handling means for selectively directing a liquid sample from main micro-channel 552 to either of first and second branch micro-channels 554 and 556. Examples of such liquid handling means include, but are not limited to, active valves, passive valves, capillary breaks, air pressure barriers and hydrophobic patches.

Configuration 550 can be employed to detect the position of a liquid sample in either first branch micro-channel 554 (by employing meter 570 to measure an electrical characteristic between first position electrode 558 and second position electrode 560) or second branch micro-channel 556 (by employing meter 570 to measure an electrical characteristic between third position electrode 562 and fourth position electrode 564). Such detection(s) can be employed to control liquid sample flow and the determination of an analyte in the liquid sample by either first analyte sensor 566 or second analyte sensor 568. A benefit of configuration 550 is that the first and second position electrodes (as well as the third and fourth position electrodes) can be positioned relatively close together to enable accurate measurements of relatively high electrical characteristics (e.g., relatively high impedances) therebetween.

Figure 13:
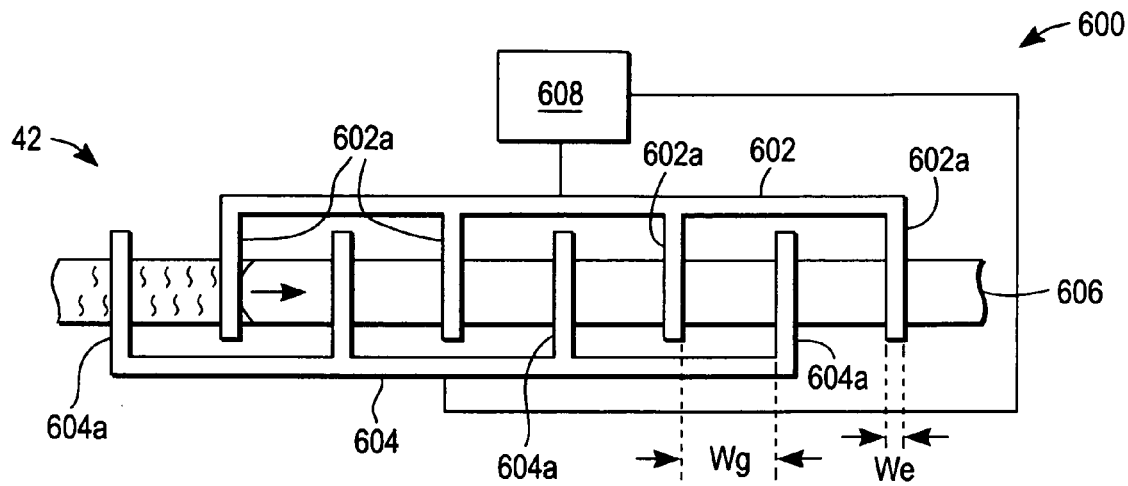
FIG. 13 is a simplified schematic diagram of a position electrode, micro-channel and meter configuration for use in embodiments of microfluidic analytical systems according to the present invention.
Figure 14:
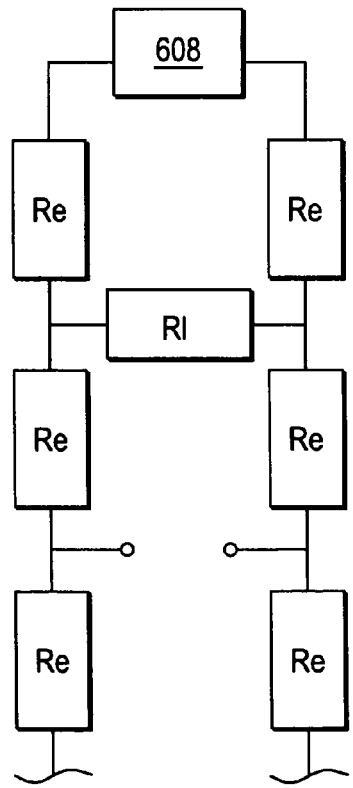
FIG. 14 is a simplified schematic diagram of an equivalent electrical circuit for a portion of the configuration of FIG. 13.

FIG. 13 is a simplified schematic diagram of a position electrode, micro-channel and meter configuration 600 for use in embodiments of microfluidic analytical systems according to the present invention. FIG. 14 is a simplified schematic diagram of an equivalent electrical circuit for a portion of configuration 600 of FIG. 13.

Configuration 600 includes a first position electrode 602 and a second position electrode 604 in an interdigitated configuration. Configuration 600 also includes a micro-channel 606 and a meter 608. First and second position electrodes 602 and 604 each having a plurality of electrode portions that are placed substantially parallel to, and in alternating succession with, each other (e.g., in an alternating, "finger-like" pattern as depicted in FIG. 13). For explanatory purposes, four electrode portions for first and second position electrodes 602 and 604 (602a and 604a, respectively) are illustrated in FIG. 13. The interdigitated electrode portions are also referred to as "fingers."

The position electrodes of embodiments of the present invention and the spacing therebetween can be of any suitable dimension. Advantageously, an interdigitated configuration can be employed with dimensions (e.g., dimensions $W_g$ and $W_e$ of FIG. 13) that allow for the measurement of electrical properties of a relatively small liquid sample.

In configuration 600, each "finger" can independently have a width $W_e$ in the range of, for example, from about 1 micrometers to about 1500 micrometers. The separation between electrode "fingers" ($W_g$) can be, for example, in the range between about 0.1 millimeters and about 15 millimeters. The thickness of the position electrodes is sufficient to support a desired electric current. Exemplary thicknesses are, for example, in the range from about 1 micrometers to about 100 micrometers.

Interdigitated configurations such as configuration 600 can have any number of "fingers" that are sufficient to provide utility, e.g., providing contact with a liquid sample and to measure an electrical characteristic. An interdigitated configuration can have, for example, from 2 to about 100 "fingers."

Configuration 600 can be employed to detect a liquid sample bolus(es) flowing through micro-channel 606. With such boluses having a pre-determined volume (such as for example 250 nanoliters) defined by the height and width of micro-channel 606 and the distance $W_g$. For example, if micro-channel 606 has a height and width that are both about 250 microns, $W_e$ is about 0.5 millimeters and $W_g$ is about 4 millimeters, then when there is no liquid sample bridging between any finger of position electrode 602 and position electrode 604, the resistance between first electrode 602 and second electrode 604 is essentially infinity. However, if an ISF liquid sample bridges (fills) micro-channel 606 between the first finger of the first position electrode and the first finger of the second position electrode (a circumstance depicted by wavy lines in FIG. 13), a measured total resistance $R_T$ decreases to a liquid resistance $R_l$ of about 37 KOhm.

It should be noted that in configuration 600, the resistance of each finger $R_e$ is much less than $R_l$ by at least about a factor of ten. As micro-channel 606 fills further with a liquid sample, the measured total resistance $R_T$ between first position electrode 602 and second position electrode 604 further decreases. The decrease in total measured total resistance $R_T$ can characterized by the equation $$R_T = \frac{R_l}{n},$$

where n=the number fingers "bridged" by the liquid sample. Configuration 600 is particularly useful when $R_e$ is much less than $R_l$.

In configuration 600, micro-channel 606 is depicted as passing (i.e., coming into operative communication with) each electrode finger 602a one time. However, micro-channel 606 could alternatively have a serpentine configuration such that micro-channel 606 passes each electrode finger 602a a plurality of times. Such a configuration can enhance the ability to easily resolve relatively small liquid sample volumes (e.g., liquid sample volumes of less than 5 nl).

Figure 15:
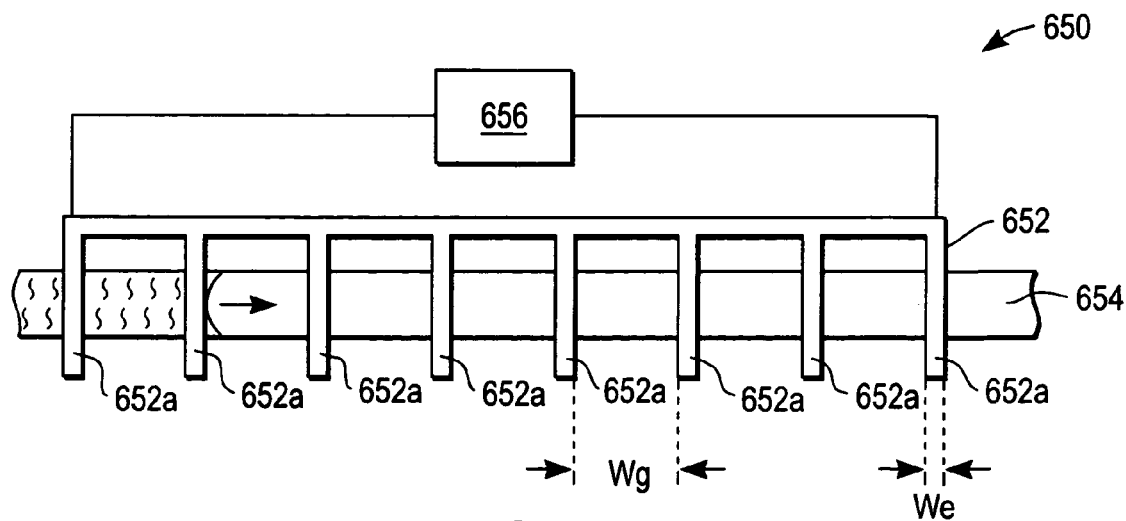
FIG. 15 is a simplified schematic diagram of a further position electrode, micro-channel and meter configuration for use in embodiments of microfluidic analytical systems according to the present invention.
Figure 16:
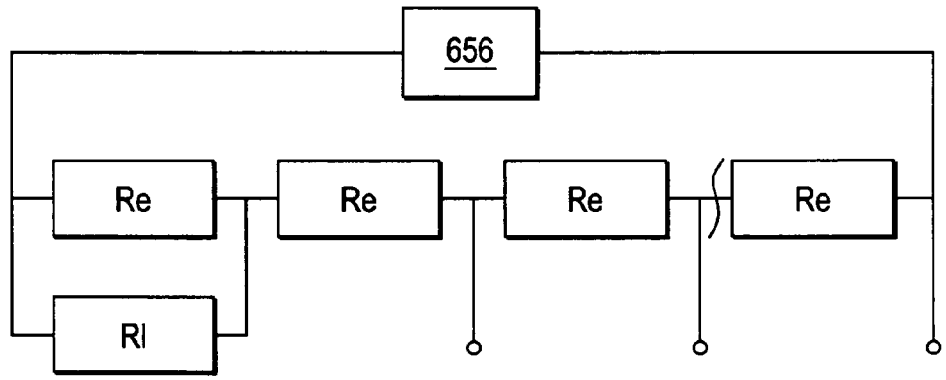
FIG. 16 is a simplified schematic diagram of an equivalent electrical circuit for a portion of the configuration of FIG. 15.

FIG. 15 is a simplified schematic diagram of a position electrode, micro-channel and meter configuration 650 for use in embodiments of microfluidic analytical systems according to the present invention. FIG. 16 is a simplified schematic diagram of an equivalent electrical circuit for a portion of configuration 600 of FIG. 15.

Configuration 650 includes a single comb-shaped position electrode 652 with eight "fingers" 652a, a micro-channel 654 and a meter 656. Electrode fingers 652a serve to define electrode segments therebetween with each segment having a resistance $R_e$ (as depicted in FIG. 16). It should be noted that the dimensions $W_g$ and $W_e$ of FIG. 16 can be the same as described previously with respect to configuration 600.

When there is no liquid sample in micro-channel 654 between any of the eight fingers 652a, a measured total resistance of position electrode 652 is the summation of the resistance for each electrode segment $R_e$ (i.e., the resistance of all electrode elements together). However, once a liquid sample begins to fill micro-channel 654 between any of fingers 652a, the measured total resistance $R_T$ decreases since resistance $R_I$ is created in parallel to $R_e$ (see FIG. 16). It should be noted that with respect to configuration 650, the resistance of each electrode segment $R_e$ is significantly greater than $R_I$, preferably by about a factor of ten or greater.

Figure 17:
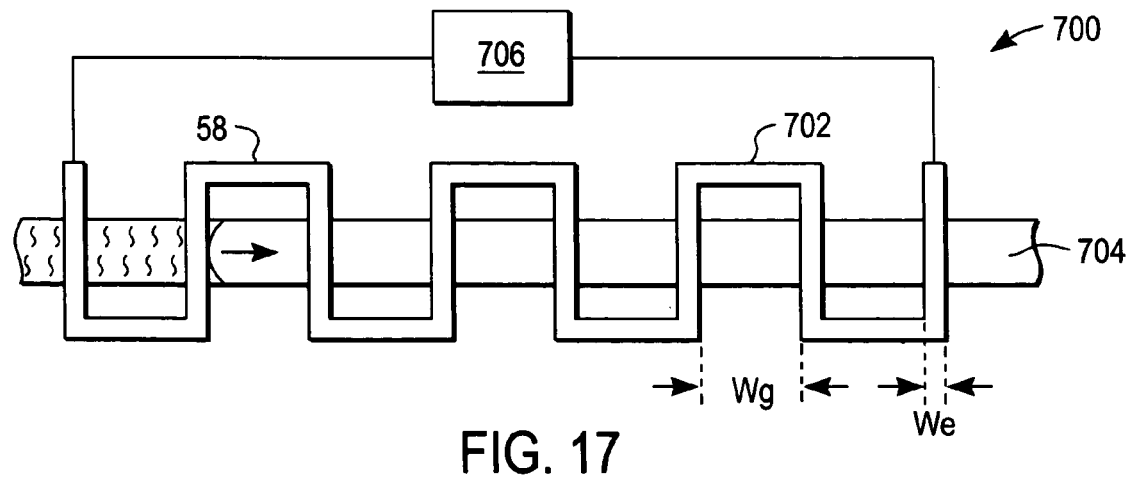
FIG. 17 is a simplified schematic diagram of another position electrode, micro-channel and meter configuration for use in embodiments of microfluidic analytical systems according to the present invention.

FIG. 17 is a simplified schematic diagram of a position electrode, micro-channel and meter configuration 700 for use in embodiments of microfluidic analytical systems according to the present invention. Configuration 700 includes a single serpentine-shaped position electrode 702, a micro-channel 704 and a meter 706.

It should be noted that the dimensions $W_g$ and $W_e$ of FIG. 16 can be the same as described previously with respect to configuration 600.

Figure 18:
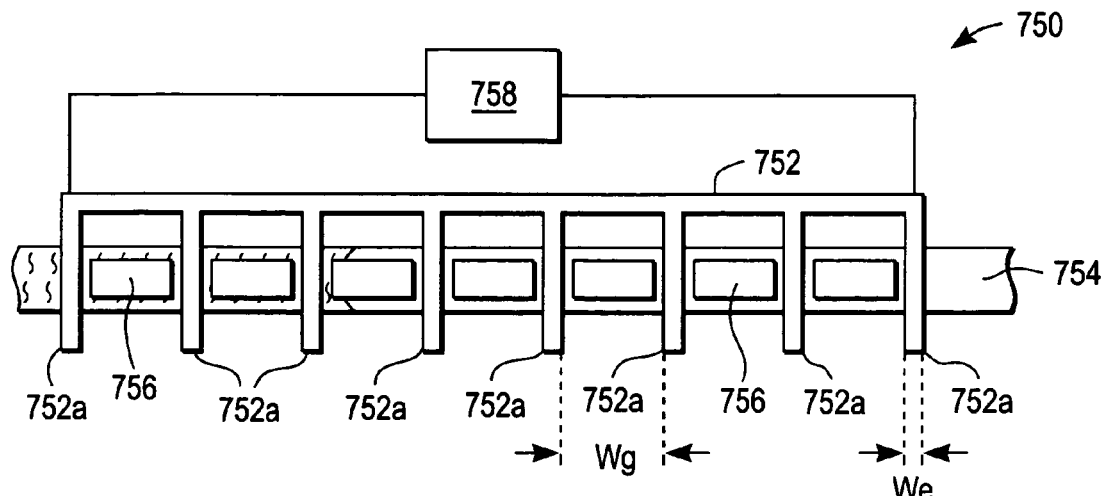
FIG. 18 is a simplified schematic diagram of yet another position electrode, micro-channel and meter configuration for use in embodiments of microfluidic analytical systems according to the present invention.
Figure 19:
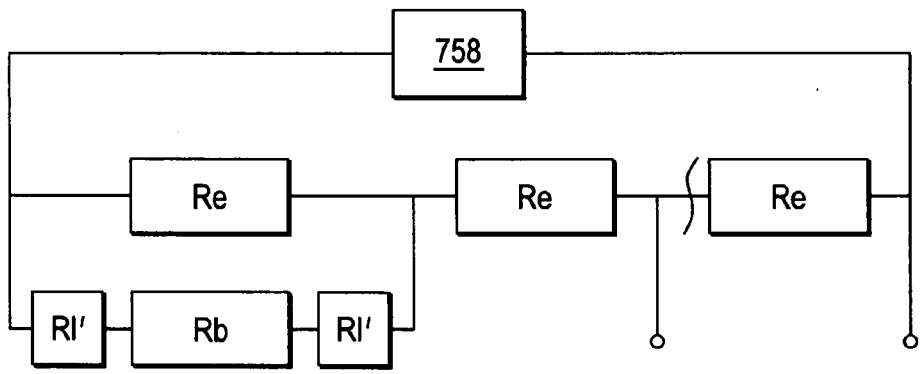
FIG. 19 is a simplified schematic diagram of an equivalent electrical circuit for a portion of the configuration of FIG. 18.

FIG. 18 is a simplified schematic diagram of a position electrode, micro-channel and meter configuration 750 for use in embodiments of microfluidic analytical systems according to the present invention. FIG. 19 is a simplified schematic diagram of an equivalent electrical circuit for a portion of configuration 750 of FIG. 18.

Configuration 750 includes a position electrode 752, micro-channel 754, bypass electrode 756, and meter 758. Position electrode 752 is a single comb-shaped position electrode with eight electrode "fingers" 752a. Electrode fingers 752a serve to define electrode segments therebetween with each segment having a resistance $R_e$ (as depicted in FIG. 18). It should be noted that the dimensions $W_g$ and $W_e$ of FIG. 18 can be the same as described previously with respect to configuration 600.

In the absence of any liquid sample, bypass electrode 756 is electrically floating. However, when a liquid sample is present between two consecutive electrode fingers 752a, bypass electrode 756 becomes a part of the circuit depicted in FIG. 19 and is characterized by resistance $R_b$.

Assuming that $R_b$ is significantly less than $R_I'$ (i.e., the resistance of a liquid sample between an electrode finger and a bypass electrode), more current will flow through the bypass electrode than the liquid sample. Therefore, configuration 750 is beneficial when used in combination with high-resistive liquid samples since bypass electrode 756 effectively reduces the $R_T$, as shown schematically in FIG. 19. Furthermore, once apprised of the present disclosure, one skilled in the art will recognize that a bypass electrode(s) can be similarly disposed between position electrodes or between electrode fingers in a variety of electrode configurations (for example, the configurations of FIGS. 7, 9–13 and 17) to reduce total measured resistance in the presence of a relatively high-resistive liquid sample.

Figure 20:
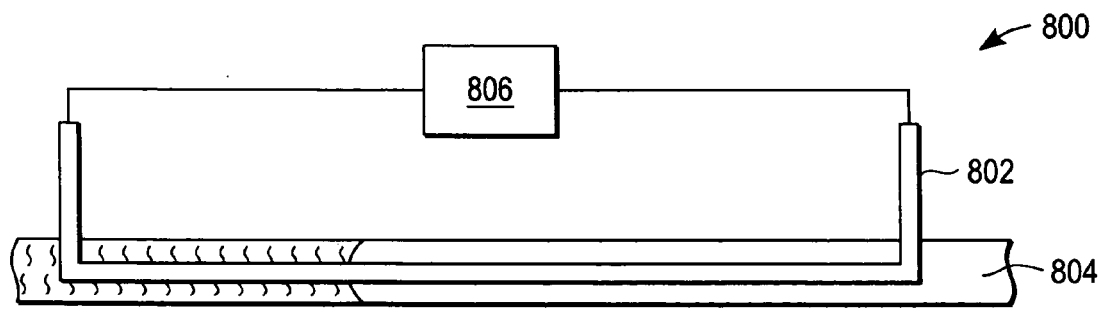
FIG. 20 is a simplified schematic diagram of still another a position electrode, micro-channel and meter configuration for use in embodiments of microfluidic analytical systems according to the present invention.

FIG. 20 is a simplified schematic diagram of a position electrode, micro-channel and meter configuration 800 for use in embodiments of microfluidic analytical systems according to the present invention. Configuration 800 includes a position electrode 802, micro-channel 804 and meter 806. Meter 806 is configured to measure a continually changing electrical characteristic of position electrode 802 as a liquid sample (depicted by the wavy lines in FIG. 20) passes through micro-channel 804.

EXAMPLE

An interdigitated configuration similar to that of FIG. 13 was tested by employing a phosphate buffer solution as a liquid sample. The first and second position electrodes of the configuration were formed from Ag/AgCl using a screen printing technique. In addition, the first position electrode and second position electrode were separated by a distance $W_g$ of 4 millimeters.

Figure 21:
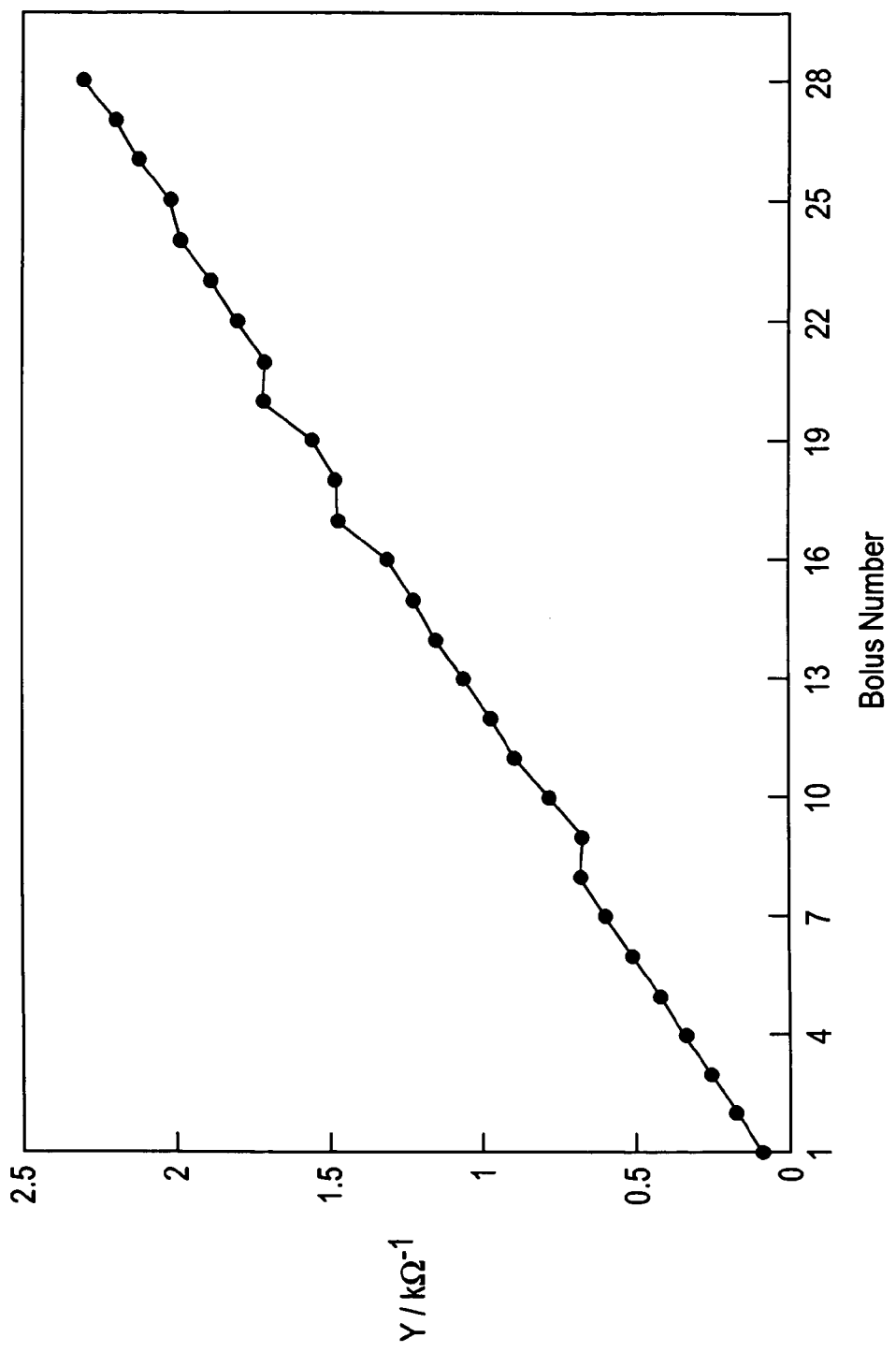
FIG. 21 is a graph of admittance versus bolus number.

A potential waveform was applied between the first and second position electrodes with a frequency of 0.25 MHz, an amplitude of +/−0.1 volts, and a RMS of 0 volt. Based on the resulting current between the first and second position electrodes, measured total resistance $R_T$ and total measured admittance were calculated (it should be noted that $A_T=1/R_T$). FIG. 21 shows that the measured total admittance $A_T$ increases linearly as successive liquid sample boluses pass each of the electrode fingers of the configuration.

FIG. 21 illustrates that each successive bolus was detected as a change in admittance. Therefore, boluses can be counted by, for example, monitoring for spikes in the derivative of a measured impedance signal versus time.

It should be understood that various alternatives to the embodiments of the invention described herein may be employed in practicing the invention. It is intended that the following claims define the scope of the invention and that structures within the scope of these claims and their equivalents be covered thereby.

What is claimed is:

1. A microfluidic analytical system for monitoring an analyte in a liquid sample, the microfluidic analytical system comprising:
    an analysis module including
        at least one micro-channel for receiving and transporting a liquid sample;
        at least one analyte sensor for measuring an analyte in the liquid sample, each of the at least one analyte sensors being in operative communication with a micro-channel; and
        at least one position electrode, each of the at least one position electrodes in operative communication with at least one micro-channel; and
    a meter configured for measuring an electrical characteristic of the at least one position electrode, the electrical characteristic being dependent on a position of the liquid sample in the micro-channel in operative communication with the at least one position electrode for which an electrical characteristic is measured.

2. The microfluidic analytical system of claim 1 further including a timer in operative communication with the meter.

3. The microfluidic analytical system of claim 1, wherein the position electrode is in operative communication with the micro-channel such that a surface of the position electrode is exposed to the micro-channel.

4. The microfluidic analytical system of claim 1, wherein the position electrode is in operative communication with the micro-channel such that an insulating layer separates the position electrode from the micro-channel.

5. The microfluidic analytical system of claim 1, wherein the at least one position electrode includes a first position electrode and a second position electrode with the first and second position electrodes in operative communication with a first micro-channel; and
    wherein the meter is configured for measuring an electrical characteristic between the first and the second position electrode.

6. The microfluidic analytical system of claim 5, wherein the analyte sensor is disposed between the first position electrode and a second position electrode.

7. The microfluidic analytical system of claim 5, wherein the first position electrode and the second position electrode are downstream of the analyte sensor.

8. The microfluidic analytical system of claim 5, wherein the electrical characteristic is at least one of an impedance between the first and second position electrodes and a resistance between the first and second position electrodes.

9. The microfluidic analytical system of claim 1, wherein the at least one position electrode is in operative communication with the analyte sensor.

10. The microfluidic analytical system of claim 5 further including a third position electrode in operative communication with the first micro-channel and wherein the meter is configured for measuring an electrical characteristic between any two of the first, second and third position electrodes.

11. The microfluidic analytical system of claim 1, wherein the micro-channel includes at least one main micro-channel and at least a first and a second branching micro-channel.

12. The microfluidic analytical system of claim 11, wherein the at least one position electrode includes at least one position electrode in the main micro-channel, at least one position electrode in the first branching micro-channel and at least one position electrode in the second branching micro-channels and
   wherein the meter measures an electrical characteristic between the position electrode in the main micro-channel and either of the position electrodes in the first and second branching micro-channels.

13. The microfluidic analytical system of claim 11, wherein the at least one position electrode includes at least two position electrodes in the first branching micro-channel and at least two position electrodes in the second branching micro-channels and
   wherein the meter measures an electrical characteristic between either of the two position electrodes in the first branching micro-channel and the two position electrodes in the second branching micro-channel.

14. The microfluidic analytical system of claim 11, wherein the at least one position electrode includes a first and second position electrode configured in an interdigitated configuration.

15. The microfluidic analytical system of claim 11, wherein the at least one position electrode is a serpentine position electrode.

16. The microfluidic analytical system if claim 1 further including a bypass electrode.

* * * * *

UNITED STATES PATENT AND TRADEMARK OFFICE
Certificate

Patent No. 6,990,849 B2            Patented: January 31, 2006

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Sebastian Bohm, Inverness (GB); James Iain Rodgers, Lochardil (GB); Alan McNeilage, Inverness (GB); James Moffat, Inverness (GB); Matthias Stiene, Inverness (GB); Tanja Richter, Inverness (GB); Geoffrey Lillie, Inverness (GB).

Signed and Sealed this Eleventh Day of March 2008.

HEZRON E. WILLIAMS
*Supervisory Patent Examiner*
Art Unit 2856